United States Patent
Knauf et al.

(10) Patent No.: US 10,689,322 B2
(45) Date of Patent: Jun. 23, 2020

(54) PROCESS FOR PREPARATION OF DI- AND POLYAMINES OF THE DIPHENYLMETHANE SERIES

(71) Applicant: Covestro Deutschland AG, Leverkusen (DE)

(72) Inventors: Thomas Knauf, Dormagen (DE); Stefan Wershofen, Mönchengladbach (DE); Klaus-Gerd Gruner, Duisburg (DE); Volker Hartjes, Duisburg (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 15/317,482

(22) PCT Filed: Jun. 22, 2015

(86) PCT No.: PCT/EP2015/063934
§ 371 (c)(1),
(2) Date: Dec. 9, 2016

(87) PCT Pub. No.: WO2015/197527
PCT Pub. Date: Dec. 30, 2015

(65) Prior Publication Data
US 2017/0137367 A1    May 18, 2017

(30) Foreign Application Priority Data
Jun. 24, 2014 (EP) .................... 14173580

(51) Int. Cl.
*B01J 19/00* (2006.01)
*C07C 209/78* (2006.01)
(Continued)

(52) U.S. Cl.
CPC ............ *C07C 209/78* (2013.01); *B01D 17/02* (2013.01); *B01J 14/00* (2013.01); *B01J 19/0006* (2013.01);
(Continued)

(58) Field of Classification Search
CPC .................................................. C07C 209/78
See application file for complete search history.

(56) References Cited

U.S. PATENT DOCUMENTS 3,297,759 A * 1/1967 Curtiss ................... C08G 12/08
564/333
3,517,062 A * 6/1970 Powers ................. C07C 209/78
528/64

(Continued)

FOREIGN PATENT DOCUMENTS

DE  844896  9/1952
EP  1167343 A1 * 1/2002 ........... C07C 209/78
(Continued)

OTHER PUBLICATIONS

Translation of EP 1167343 A1 by Schreiber Translations, Inc. Aug. 2019. (Year: 2019).*
(Continued)

*Primary Examiner* — Jennifer A Leung
(74) *Attorney, Agent, or Firm* — Donald R. Palladino

(57) ABSTRACT

The present invention relates to a process for preparing di- and polyamines of the diphenylmethane series (MDA), a system for producing MDA and a process for operating a system for preparing MDA. The invention enables optimization of production standstills during operation of the MDA process with respect to time expenditure and optionally also with respect to energy and material consumption by means of a so-called recirculation mode for individual system components. During interruption of the process or interrup-
(Continued)

tion of the operation of individual system components, formaldehyde is not introduced into the reaction and the system components that are not affected by a revision, repair, or cleaning measure are operated in so-called recirculation mode. This enables, among other things, that only the affected system component can be put in standstill during the time period of the measure, which is advantageous in terms of productivity and economy of the process as well as in terms of the quality of the products produced.

13 Claims, 2 Drawing Sheets

(51) Int. Cl.

| | | |
|---|---|---|
| *B01L 3/14* | (2006.01) | |
| *B01D 17/02* | (2006.01) | |
| *B01J 14/00* | (2006.01) | |
| *B01J 19/24* | (2006.01) | |
| *C02F 1/04* | (2006.01) | |
| *C07C 209/84* | (2006.01) | |
| *C07C 209/86* | (2006.01) | |
| *C02F 101/38* | (2006.01) | |
| *C02F 103/36* | (2006.01) | |

(52) U.S. Cl.
CPC ............ *B01J 19/245* (2013.01); *B01L 3/14* (2013.01); *C02F 1/04* (2013.01); *C07C 209/84* (2013.01); *C07C 209/86* (2013.01); *B01J 2219/00225* (2013.01); *C02F 2101/38* (2013.01); *C02F 2103/36* (2013.01); *Y02P 20/582* (2015.11)

(56) References Cited

U.S. PATENT DOCUMENTS

| | | | | |
|---|---|---|---|---|
| 3,954,867 A | * | 5/1976 | Funk, Jr. | ............ 564/333 |
| 4,290,110 A | * | 9/1981 | Makovec | ............ B01J 8/001 |
| | | | | 422/111 |
| 4,792,624 A | | 12/1988 | Hatfield, Jr. et al. | |
| 4,914,236 A | | 4/1990 | Knofel et al. | |
| 5,053,539 A | | 10/1991 | Yano et al. | |
| 5,286,760 A | | 2/1994 | Bolton et al. | |
| 6,433,219 B1 | | 8/2002 | Ströfer et al. | |
| 6,576,788 B1 | | 6/2003 | Penzel et al. | |
| 6,649,798 B2 | | 11/2003 | Klein et al. | |
| 7,186,857 B2 | | 3/2007 | Müller et al. | |
| 7,230,130 B2 | | 6/2007 | Ströfer et al. | |
| 7,253,321 B2 | | 8/2007 | Hagen et al. | |
| 7,312,362 B2 | | 12/2007 | Keggenhoff et al. | |
| 7,528,283 B2 | | 5/2009 | Pohl et al. | |
| 9,138,717 B2 | | 9/2015 | Ding et al. | |
| 9,217,054 B2 | | 12/2015 | Carr et al. | |
| 2006/0111575 A1 | * | 5/2006 | DeCourcy | ............ B01J 19/002 |
| | | | | 549/248 |
| 2009/0240077 A1 | | 9/2009 | Wershofen et al. | |

FOREIGN PATENT DOCUMENTS

| | | | | |
|---|---|---|---|---|
| EP | 2039676 A1 | * | 3/2009 | ............ C07C 209/78 |
| GB | 1228495 A | * | 4/1971 | ............ B01J 19/1862 |

OTHER PUBLICATIONS

Twitchett, H. J.; Chem. Soc. Rev. 3(2); (1974); "Chemistry of the Production of Organic Isocyanates"; pp. 209-230.

Treybal, Robert E.; Mass-Transfer Operations; Third Edition; (1980); McGraw-Hill Book Co.; pp. 477-541.

Müller, E. et al; Ullmann's Encyclopedia of Industrial Chemistry; "Liquid-Liquid Extraction"; vol. 21; pp. 272-274; (2012); Wiley VCH Verlag GmbH & Co. KGaA, Weinheim, DOI: 10.1002/14356007.b03_06.pub2.

Kirk-Othmer Encyclopedia of Chemical Technology (see "http://onlinelibrary.wiley.com/book/10.1002/0471238961"); John Wiley & Sons, Inc.; Extraction, Liquid-Liquid; pp. 22-23 (mixer-settler cascades or settling vessels); Published Online: Jun. 15, 2007.

* cited by examiner

PROCESS FOR PREPARATION OF DI- AND POLYAMINES OF THE DIPHENYLMETHANE SERIES

CROSS-REFERENCE TO RELATED APPLICATIONS

This Application is a National Phase Application of PCT/EP2015/063934, filed Jun. 22, 2015, which claims priority to European Application No. 14173580.3, filed Jun. 24, 2014, each of which being incorporated herein by reference.

FIELD

The present invention relates to a process for preparing diamines and polyamines of the diphenylmethane series (MDA), a plant for preparing MDA and a method of operating a plant for preparing MDA. The invention makes it possible to optimize production stoppages during operation of the MDA process in respect of time taken and optionally also in respect of energy and materials consumption by means of a circulatory mode of operation of individual plant parts. During interruption of the process or interruption of operation of individual plant parts, no formaldehyde is introduced into the reaction and the plant parts not affected by an inspection, repair or cleaning measure are operated in the circulatory mode of operation. As a result, inter alia, only the plant part affected has to be shut down for the duration of the measure, which can be advantageous in respect of productivity and economics of the process and also the quality of the products produced.

BACKGROUND

The continuous or partially batchwise preparation of MDA is, for example, described in EP 1 616 890 A1, U.S. Pat. No. 5,286,760, EP-A-451442 and WO-A-99/40059. The acidic condensation of aromatic amines and formaldehyde to form diamines and polyamines of the diphenylmethane series proceeds in a plurality of reaction steps.

In the aminal process, formaldehyde is firstly condensed with aniline in the absence of an acid catalyst to form aminal, with water being eliminated. The rearrangement to form MDA is then carried out in the presence of an acid catalyst in a first step to form para- and ortho-aminobenzylaniline. The aminobenzylanilines rearrange to form MDA in a second step. Main products of the acid-catalyzed reaction of aniline and formaldehyde are the diamine 4,4'-MDA, its positional isomers 2,4'-MDA and 2,2'-MDA and also higher homologues.

In the neutralization process, aniline and formaldehyde are converted directly in the presence of an acid catalyst into aminobenzylanilines which subsequently react further to form the two-ring MDA isomers and MDA homologues having more than two rings.

Regardless of the process variant for preparing the acidic reaction mixture, the work-up of the latter is commenced by neutralization by means of a base in the prior art. The neutralization is usually carried out at temperatures of, for example, from 90° C. to 100° C. without addition of further substances (H. J. Twitchett, Chem. Soc. Rev. 3(2), 223 (1974)). However, it can also be carried out at a different temperature level, for example to accelerate the degradation of interfering by-products. Hydroxides of the alkali and alkaline earth elements are suitable as bases. Preference is given to using aqueous NaOH.

After the neutralization, the organic phase is separated from the aqueous phase in a separation vessel. The organic phase containing crude MDA which remains after the aqueous phase has been separated off is subjected to further work-up steps, e.g. washing with water (base wash) in order to wash residual salts out of the crude MDA. The crude MDA which has been purified in this way is subsequently freed of excess aniline, water and other materials present in the mixture (e.g. further solvents) by suitable methods such as distillation, extraction or crystallization. The work-up customary in the prior art is disclosed, for example, in EP 1 652 835 A1, page 3, line 58 to page 4, line 13, or EP 2 103 595 A1, page 7, lines 21 to 37.

EP 1 616 890 A1 teaches that aniline and formaldehyde are firstly reacted in the absence of the acid catalyst to form aminal and the aminal is subsequently admixed with the acid catalyst and is reacted further at temperatures of from 20° C. to 100° C. and water contents of the acidic reaction mixture obtained in this way of from 0 to 20 percent by weight. In particular, the water is firstly at least partly removed from the aminal after the condensation of formaldehyde and aniline, with a water content of from 0 to 5 percent by weight being set in the aminal, and the aminal is subsequently admixed with acid catalyst and is reacted further at temperatures of from 20° C. to 100° C. and water contents of the acidic reaction mixture obtained in this way of from 0 to 20 percent by weight. Mixtures of the diamines and polyamines of the diphenylmethane series can in this way be produced at degrees of protonation of <15%, preferably from 4% to 14%, particularly preferably from 5% to 13%. Here, the degree of protonation is in the case of monoprotic acid catalysts (e.g. hydrochloric acid) the molar ratio of the amount of acid catalyst used and the molar amount of amine functions present in the reaction mixture. The patent application does not give any details concerning the procedure during shutdown of individual plant parts of an industrial production plant. The examples present therein are laboratory experiments. In particular, this patent application does not teach that merely individual plant parts and not necessarily the entire plant have to be completely rundown in order to effect shutdown.

The patent application EP 2 039 676 A1 is concerned with the preparation of MDA with the focus on neutralization and washing. It describes a mode of operation for optimizing the phase separation in the neutralization (step c) and/or washing (step e2). Part of the aqueous phase from the phase separation in the washing step e2) or the separation of aminal from the wastewater e3) is returned to the neutralization or washing. In other words: the configuration of an MDA plant in continuous normal operation is described. A procedure in the case of a shutdown of the MDA plant in which individual plant parts are taken out of operation and other plant parts are operated in the circulatory mode of operation is not disclosed in the patent application.

EP 0 283 757 A1 is likewise concerned with the preparation of MDA. The process described is characterized by the addition of aniline-free MDA's to aminobenzylamines formed by condensation of aniline and formaldehyde before they are rearranged in a reaction induced by heat. Example 2 describes a mode of operation in which a small part of the MDA formed is recirculated to the rearrangement reaction (cf. also claims 6 and 8). In other words: the configuration of an MDA plant in continuous normal operation is described. Details regarding the procedure when individual plant parts are shut down are not disclosed in the patent application.

WO-A-99/40059 teaches that in order to prepare methylenedi(phenylamine) by reaction of aniline with formaldehyde in the presence of acid catalysts in a semicontinuous process, aniline and optionally acid catalyst are initially charged, formaldehyde and optionally acid catalyst are fed through a mixing device into a circuit in which aniline, optionally acid catalyst and optionally previously introduced formaldehyde are circulated and the reaction mixture is brought to a temperature of greater than 75° C. after at least 50% of the total amount of formaldehyde to be introduced has been fed in. The introduction up to an amount of at least 50% of the total amount of formaldehyde to be introduced is carried out at a temperature of the reaction mixture in the circuit of from 20° C. to 75° C.

The quality of a process for preparing MDA is defined firstly by the content of undesirable by-products of the reaction in the product. Secondly, the quality of a process is defined by the overall process from start-up, normal production to running-down of the process being able to be operated without technical production failure or problems which require intervention in the process and by no losses of starting materials, intermediates or end product occurring.

Such problems can, for example, occur during start-up or running-down of the aminal reaction. Such problems can be, for example, high molecular weight solids being formed and leading to caking and blockages in the equipment (aminal vessel, aminal cooler and aminal separator and conduits). A further disadvantage is that all plant parts normally always have to be shut down when maintenance, repair and cleaning work is necessary on or in a reactor or another plant part since the process steps build on one another and are therefore always carried out in succession. As a result, the entire plant has to be emptied, which leads to a considerable amount of rejected material. Furthermore, energy has to be expended in order to bring reactors and plant parts back to the respective operating temperatures. Such production stoppages for plant inspections, repair measures and cleaning measures or shortage of raw materials or auxiliaries, planned or unplanned, are therefore always recurring plant states which have a considerable influence on the economical operation of a continuously operating plant or a continuously operating process.

SUMMARY

Although the processes which have been described in the prior art make it possible to produce MDA in high yield without a deterioration in quality of the end products, only processes which are in normal operation are described. Processes or plants which take sufficient account of production stoppages for plant inspections, repair measures or, for example, shortage of raw material or auxiliaries have hitherto not been described in the prior art. It would thus be desirable to have processes and plants for preparing diamines and polyamines of the diphenylmethane series in which it is possible to optimize production stoppages during operation of the MDA process in respect of time taken and optionally also in respect of energy and materials consumption. These would lead to a not inconsiderable extent to an improvement in productivity and thus the economics of a continuously operating MDA production process and the corresponding plants.

The present invention therefore provides the following:

A process for preparing diamines and polyamines of the diphenylmethane series (MDA), which comprises the steps: in a variant A)

IA) reaction of aniline and formaldehyde in the absence of an acid catalyst in a reactor to form an aminal, with aniline being introduced at a mass flow rate $m_1$ and formaldehyde being introduced at a mass flow rate $m_2$ into the reactor, followed by separation of the reaction mixture obtained into an aqueous phase and an organic phase containing the aminal in a phase separation facility integrated into the reactor or in a separate phase separation apparatus (known as the "aminal separator");

IIA) reaction of at least part of the organic phase containing the aminal which is obtained in step IA) with acid in a reactor, with the aminal reacting to form diamines and polyamines of the diphenylmethane series;

("aminal process");

or in a variant B)

IB) reaction of aniline and acid in a reactor;

IIB) reaction of at least part of the reaction mixture obtained in step IB) with formaldehyde in a reactor to form diamines and polyamines of the diphenylmethane series, with the aniline-containing reaction mixture from step IB) being introduced at a mass flow rate $m_1$ and formaldehyde being introduced at a mass flow rate $m_2$ into the reactor of step IIB);

("neutralization process")

and (for both variants A) and B)) the optional steps III) to VIII)

III) neutralization of the reaction mixture obtained in step IIA) or IIB) in a reactor;

IV) separation of the neutralized reaction mixture obtained in step III) into an organic phase comprising diamines and polyamines of the diphenylmethane series and an aqueous phase in a separation vessel;

V) washing of the organic phase with washing liquid in a washing vessel;

VI) separation of the mixture obtained in step V) into an organic phase comprising diamines and polyamines of the diphenylmethane series and an aqueous phase in a separation vessel;

VII) distillation of the organic phase from step VI), with diamines and polyamines of the diphenylmethane series being separated off from water and aniline, giving a stream containing water and aniline;

VIII) work-up of the aqueous phase from step IA) and/or the aqueous phase from step IV) and/or the aqueous phase from step VI) and/or the stream containing water and aniline from step VII) in a wastewater work-up facility which preferably comprises a wastewater collection vessel, wastewater heater and aniline separation vessel, with in the case of a plurality of aqueous phases or streams to be worked up these preferably being combined in the wastewater collection vessel and fed jointly to further work-up, wherein in the case of a shutdown of one or more plant parts of steps I) to VII), if these are carried out, the mass flow rate $m_2$ in step (IA) or in step (IIB) is reduced to zero and the output stream from at least one of the plant parts which have not been shut down is reused as feed stream to the respective plant part or an upstream plant part.

The present invention further provides a plant for preparing diamines and polyamines of the diphenylmethane series, as is described in detail below and which is suitable for carrying out the process of the invention.

DETAILED DESCRIPTION

Figure 1:
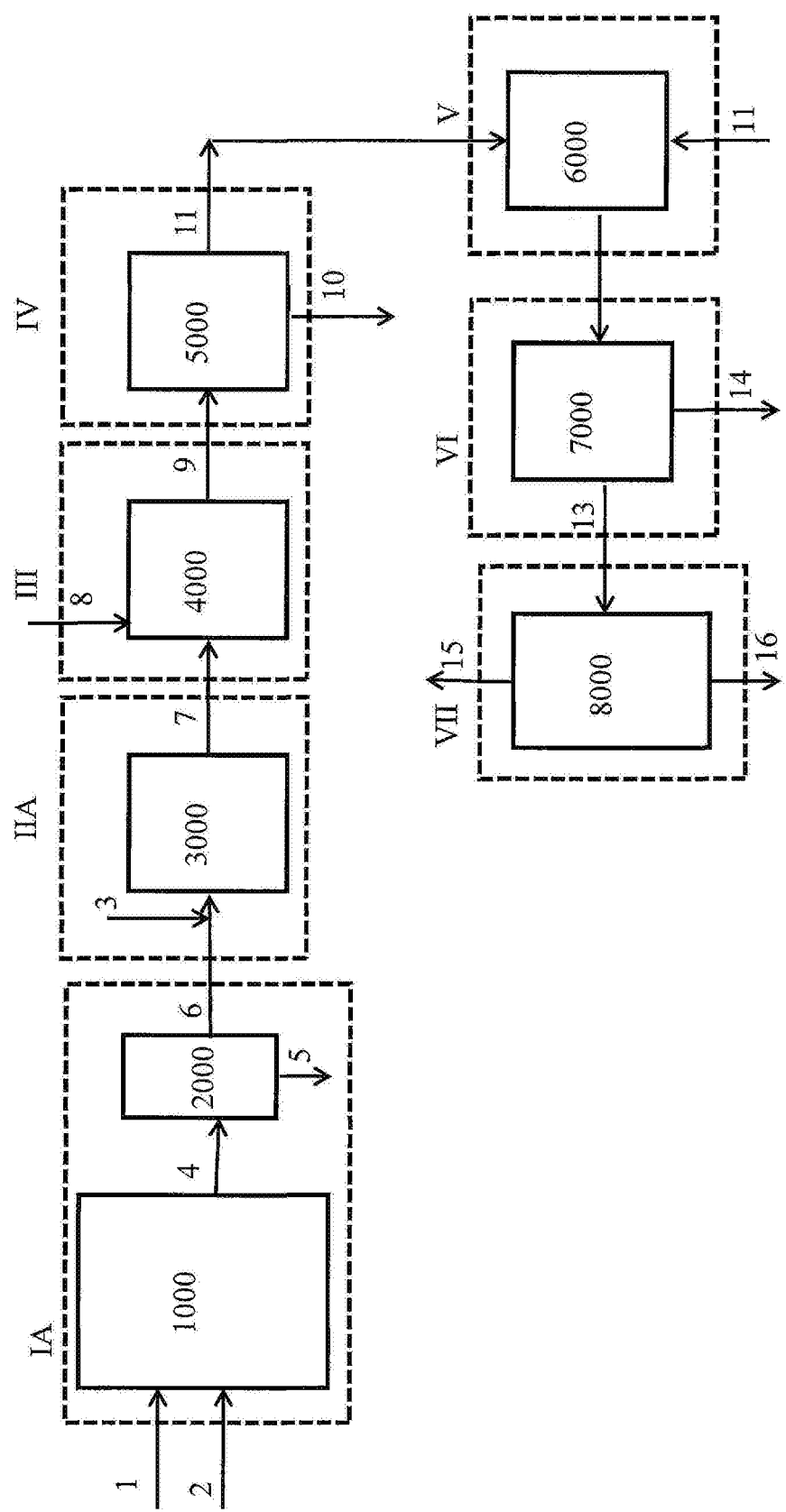
FIG. 1 is a flow diagram illustrating general conditions for the preparation of MDA in a "run-in" production plant.

Finally, the present invention provides a method of operating a plant for preparing diamines and polyamines, which is described in detail below.

In the following, the steps IA), IB), IIA) and IIB) will also be dealt with together under the collective terms I) and II), insofar as this is possible.

For the purposes of the present invention, "diamines and polyamines of the diphenylmethane series" are amines and mixtures of amines of the following type:

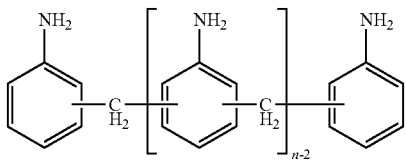

Here, n is a natural number of ≥2. In the following, the compounds of this type in which n=2 are also referred to as diamines of the diphenylmethane series or diaminodiphenylmethanes (hereinafter MMDA). Compounds of this type in which n is ≥2 will for the purposes of the present invention also be referred to as polyamines of the diphenylmethane series or polyphenylenepolymethylenepolyamines (hereinafter PMDA). Mixtures of the two types are also referred to as diamines and polyamines of the diphenylmethane series (hereinafter MDA). In industry, the diamine and polyamine mixtures are predominantly converted by phosgenation into the corresponding diisocyanates and polyisocyanates of the diphenylmethane series.

The "shutdown" of a plant part refers to the stoppage thereof, so that an inspection, repair, maintenance or cleaning measure can be carried out in the plant part. The present invention makes it possible for the entire production plant not to have to be shut down in the event of such a measure. Rather, the present invention makes it possible for plant parts not affected by the inspection, repair, maintenance or cleaning measure or the corresponding process steps to be operated in the "circulatory mode of operation". For the purposes of the present invention, when m plant parts within the meaning of the present invention (see also the next paragraph) are present, where "m" is a natural number, the term "shutdown" encompasses the shutdown of a maximum of m−1 of these plant parts. Thus, according to the invention, at least one plant part is not "shut down" (i.e. "completely stopped"). The present invention is therefore preferably concerned with the case of 1 or 2 plant parts being shut down, particularly preferably 1 plant part. According to the invention, when a plant part (or a plurality of plant parts, but not all plant parts) is shut down, the formation of further product is therefore in any case interrupted (since the mass flow rate $m_2$ is reduced to zero and no further product can therefore be produced). However, the invention also encompasses the case where the reactor of step (I) is operated in the circulatory mode of operation (see also the following paragraph) and another plant part is "shut down" within the meaning of the abovementioned definition.

For the purposes of the present invention, a "circulatory mode of operation" means that the output stream from one plant part is used as feed stream to this plant part or another plant part located upstream of the plant part concerned (i.e. is located hydrodynamically before the latter). Here, the expression "plant part" refers to the plant part corresponding to the respective step (I) to (VII), insofar as these are carried out, in a plant for preparing diamines and polyamines of the diphenylmethane series (MDA) by the process of the invention. Thus, for example, the plant part of step (I) comprises "a reactor", where this term also encompasses embodiments in which a plurality of reactors (e.g. a cascade of a plurality of reactors connected in series) are used (in other words, the word "a" is in this context and in connection with other apparatuses to be interpreted as the indefinite article and not as an indication of number). Reactors connected in parallel or in series are also known in the prior art for the preparation of MDA and can also bring advantages in particular dimensions and operational details. The plant of the invention and the process of the invention therefore also provides preferred embodiments in which reactors connected in series or in parallel are preferably employed, especially for steps (IA), (IIA), (IB), (IIB).

The circulatory mode of operation can also be set over a plurality of apparatuses of a plant part. For example, the output stream from the last apparatus of a plurality of apparatuses connected in series in a particular plant part can be used as feed stream to the first apparatus of the apparatuses connected in series of this plant part. It is also possible to employ the circulatory mode of operation only in part of the apparatuses of a plant part, e.g. when the output stream from the last apparatus of a plurality of apparatuses connected in series in a plant part is not recirculated to the first apparatus but to a further apparatus of this plant part.

The circulatory mode of operation can also be set over a plurality of plant parts. For example, the output stream from the last apparatus of a plant part, e.g. the separation vessel of step IV), can be used as feed stream to the first apparatus of an upstream plant part, e.g. the neutralization reactor of step III), with the circulatory mode of operation being set by the output stream from the neutralization separation vessel mentioned by way of example then serving as feed stream to the neutralization reactor.

Embodiments of the invention are described below. They can be combined with one another in any way, unless the contrary is clear from the context.

The steps I) and II) of the process of the invention are carried out within a continuous or semicontinuous process, preferably within a continuous process.

The shutdown of $m_2$, i.e. the flow of formaldehyde into the reactor of step IA) or IIB), ensures that the reactions in steps IA) and IIA) or in step IIB) do not continue to take place during the interruption (the shutdown of one or more plant parts) which is carried out, as described above, for the purposes of inspection, repair, maintenance and/or cleaning of part of the production plant or has been caused by a lack of raw material(s) and/or auxiliary/auxiliaries. Here, it is particularly preferred in variant A) and in variant B) that the introduction of aniline is not interrupted at the same time as the stoppage of the introduction of formaldehyde. Rather, preference is given to interrupting the introduction of further aniline with a time delay (preferably at least 10 minutes, more preferably at least 20 minutes and particularly preferably at least 30 minutes after $m_2$ has become zero) and then bringing the reactor of step IA) or of step IB) into the circulatory mode of operation, i.e. reusing the discharged reaction mixture containing aniline or the reaction product of aniline and acid as feed stream to the respective reactor. In this way, any formation of by-products can firstly be advantageously prevented and secondly, for example, formation of lumps of the reaction mixture can be prevented. Thus, contamination of the desired product, a blockage of plant parts such as pipes, valves and pumps and the production of reject material can efficiently be avoided.

In variant A), the reactor in step IA) and the reactor in step IIA) are advantageously different from one another ("aminal reactor" (step IA) and "rearrangement reactor" (step IB)). However, it is not ruled out and is also encompassed by the present invention that the reactor in step IA) and the reactor in step IB) are the same reactor.

In an alternative mode of operation according to variant B), the reaction of aniline and acid, for example hydrochloric acid, (step IB)) is advantageously carried out in a first reactor and the reaction of the reaction mixture from step IB) with formaldehyde is carried out in a second reactor (step IIB)). However, it is not ruled out and is encompassed by the present invention that the steps IB) and IIB) are carried out in the same reactor.

The process of the invention results in the following advantages:

i) An increase in the productivity because the availability of the plant is increased since the time required for running-down and restarting the plant for the production stoppage is greatly minimized.

ii) Capital costs for a larger plant capacity are not incurred.

iii) Capital costs for a larger end product tank for buffering relatively long downtimes are not incurred.

iv) Avoidance of superfluous waste products (excess aniline, crude MDA, wastewater, which additionally have to be purified) which arise when the plant has to be started up completely afresh.

v) In many cases, energy is saved because the necessary preparations for restarting the plant parts which have been shut down, e.g. heating of the starting materials and auxiliaries or heating of the equipment, etc., are dispensed with.

vi) In many cases, auxiliaries such as condensate and nitrogen are saved.

vii) The repair susceptibility of pumps or compressors is reduced since, when these are shut down in the event of a stoppage, the sliding ring seals of these suffer in every restart. Thus, subsequent repairs are avoided, which in turn has a positive effect on the productivity of the plant and the maintenance costs.

If two or more MDA production lines or reactor lines are to be operated in parallel, one or more plant parts can, according to the invention, firstly be shut down in one production line or reactor line and the other production line(s) or reactor line(s) can, if necessary, be operated according to the invention in succession in view of the shutdown of one or more associated plant parts. As an alternative, it is also possible within the framework of the present invention to operate all MDA production lines or reactor lines, if necessary, simultaneously or close to simultaneously according to the process of the invention in view of the shutdown of one or more associated plant parts.

The preparation of diamines and polyamines of the diphenylmethane series in normal operation can be summarized by way of example as follows:

in variant A)

a) key procedure of step IA): aniline and formaldehyde are condensed in the absence of an acid catalyst to form aminal and water and the resulting aminal is driven off from the aminal reactor, b) water from step a), which originates mainly from water of condensation from the aminal reaction and water from the starting material formaldehyde, is at least partly separated off as aqueous phase from the aminal reaction solution, c) key procedure of step IIA): the aminal from step b) is rearranged in the presence of an acid catalyst to form MDA, in variant B)

a') key procedure of step IB): aniline and hydrochloric acid are reacted to form a mixture of aniline and aniline hydrochloride, b') key procedure of step IIB): the mixture of aniline and aniline hydrochloride from step a') is reacted with formaldehyde to form MDA, in both variants A) and B)

d) key procedure of step III): the reaction mixture containing diamines and polyamines of the diphenylmethane series from step IIA) or step IIB) is neutralized, e) key procedure of step IV): the neutralized reaction mixture containing diamines and polyamines of the diphenylmethane series is separated in a separation vessel into an organic phase containing diamines and polyamines of the diphenylmethane series and an aqueous phase, f) key procedure of step V): the organic phase containing diamines and polyamines of the diphenylmethane series is purified further by means of washing liquid in a washing vessel, g) key procedure of step VI): the mixture obtained in this way is separated in a separation vessel into an organic phase containing diamines and polyamines of the diphenylmethane series and an aqueous phase, h) key procedure of step VII): the washed organic phase containing diamines and polyamines of the diphenylmethane series is freed of water and aniline by distillation.

The condensation of aniline and formaldehyde in a) can be carried out by a method according to the prior art. Here, aniline and aqueous formaldehyde solution are normally condensed in molar ratios in the range from 1.5 to 20, preferably from 1.5 to 10 and particularly preferably from 1.5 to 6, at temperatures of from 20° C. to 120° C., preferably from 40° C. to 110° C. and particularly preferably from 60° C. to 100° C., to form aminal and water. The reaction is usually carried out under ambient pressure. However, it can also be carried out at a slightly superatmospheric pressure. Suitable aniline grades are, for example, described in EP 1 257 522 B1, EP 2 103 595 A1 and EP 1 813 598 B1.

Preference is given to using technical grades of formalin (aqueous solution of formaldehyde) containing from 30% by mass to 50% by mass of formaldehyde in water. However, formaldehyde solutions having lower or higher concentrations or the use of gaseous formaldehyde are also conceivable.

In b), the separation of organic aminal phase and aqueous phase can be carried out at temperatures of from 20° C. to 120° C., preferably from 40° C. to 110° C., particularly preferably from 60° C. to 100° C., preferably at ambient pressure. However, the phase separation can also be carried out at a slightly superatmospheric pressure.

The rearrangement of the aminal in c) can be carried out in the presence of an acid catalyst, usually a strong mineral acid such as hydrochloric acid. Preference is given to using mineral acid in a molar ratio of mineral acid to aniline of from 0.001:1 to 0.9:1, preferably from 0.05:1 to 0.5:1. It is naturally also possible to use solid, acid catalysts as described in the literature. Here, formaldehyde can be introduced into a mixture of aniline and acid catalyst and the reaction solution can be reacted to completion by stepwise heating. As an alternative, aniline and formaldehyde can also firstly be prereacted and subsequently be, with or without prior removal of water, admixed with the acid catalyst or a mixture of further aniline and acid catalyst, after which the reaction solution is reacted to completion by stepwise heating. This reaction can be carried out continuously, semicontinuously or batchwise by one of the numerous methods described in the literature (e.g. in EP 1 616 890 A1 or EP 127 0544 A1). In d), the reaction mixture containing the diamines and polyamines of the diphenylmethane series can be neutralized, optionally with addition of water and/or aniline. According to the prior art, the neutralization is usually carried out at temperatures of, for example, from 90° C. to 100° C. without addition of further substances. However, it can also be carried out at a different temperature level, for example in order to accelerate the degradation of interfering by-products. Suitable bases are, for example, the hydroxides of the alkali and alkaline earth elements. Preference is given to using aqueous NaOH. The base used for the neutralization is preferably used in amounts of greater than 100%, particularly preferably from 105% to 120%, of the amount which is stoichiometrically required to neutralize the acid catalyst used (see EP 1 652 835 A1).

Subsequently, in e), the neutralized reaction mixture containing the diamines and polyamines of the diphenylmethane series can be separated into an organic phase containing diamines and polyamines of the diphenylmethane series and an aqueous phase. This can be assisted by the addition of aniline and/or water. If the phase separation is assisted by addition of aniline and/or water, these are preferably added with intensive mixing as early as in the neutralization. Here, mixing can be carried out in mixing sections having static mixers, in stirred vessels or cascades of stirred vessels or else in a combination of mixing sections and stirred vessels. The reaction mixture which has been neutralized and diluted by addition of aniline and/or water is subsequently preferably fed into an apparatus which, owing to its configuration and/or internals, is particularly suitable for separation into an organic phase containing MDA and an aqueous phase, preferably phase separation or extraction apparatuses corresponding to the prior art, as are described, for example, in Mass-Transfer Operations, 3rd Edition, 1980, McGraw-Hill Book Co, pp. 477 to 541, or Ullmann's Encyclopedia of Industrial Chemistry (Vol. 21, Liquid-Liquid Extraction, E. Müller et al., pages 272-274, 2012 Wiley-VCH Verlag GmbH & Co. KGaA, Weinheim, DOI: 10.1002/14356007.b03_06.pub2) or in Kirk-Othmer Encyclopedia of Chemical Technology (see "http://onlinelibrary.wiley.com/book/10.1002/0471238961", Published Online: Jun. 15, 2007, pages 22-23) (mixer-settler cascade or settling vessel).

Washing of the organic phase with water can follow in f) and renewed removal of the aqueous phase in order to remove residual contents of salt (preferably as described in DE-A-2549890, page 3) can follow in g). The organic phase obtained in step g) preferably has a composition, based on the weight of the mixture, of from 5 to 15 percent by weight of water and, depending on the ratios of aniline and formaldehyde used, from 5 to 90 percent by weight, preferably from 5 to 40 percent by weight, of aniline and from 5 to 90 percent by weight, preferably from 50 to 90 percent by weight, of diamines and polyamines of the diphenylmethane series. After exit from the phase separation in step g), the organic phase containing diamines and polyamines of the diphenylmethane series usually has a temperature of from 80° C. to 150° C.

In h), water and aniline can be separated off by distillation from the organic phase containing diamines and polyamines of the diphenylmethane series which has been obtained in g), as described in EP 1 813 597 B1.

The diamines and polyamines of the diphenylmethane series which have been obtained in this way can be reacted with phosgene by the known methods under inert conditions in an organic solvent to form the corresponding diisocyanates and polyisocyanates of the diphenylmethane series, viz. MDI. Here, the phosgenation can be carried out by one of the methods known from the prior art (e.g. DE-A-844896 or DE-A-19817691).

In a preferred embodiment, the process of the invention also comprises the steps III) to VII), particularly preferably the steps III) to VIII), both in variant A) and in variant B).

In a further preferred embodiment, the mass flow rate $m_1$ is ≥1000 kg/hour in step IA) or IB).

In a further preferred embodiment, the mass flow rate $m_2$ is ≥300 kg/hour in step (IA) or (IIB).

In both variants, the formaldehyde used can originate from any process for preparing formaldehyde known from the prior art. Merely by way of example, mention may at this point be made of the silver catalyst process.

In a further embodiment of the process of the invention, the reactor of step IA) or of step IIB) is at least partly full of aniline or the reaction product of aniline and acid. When filling the plant parts with aniline or the reaction product of aniline and acid, interruption of production can be effected in the absence of formaldehyde without formation of undesirable high molecular weight by-products.

A typical plant for preparing MDA can, according to the prior art, usually be divided into the following plant parts: a reactor for the aminal reaction (IA)) or for the reaction of aniline with acid (IB)), a reactor for the rearrangement reaction (IIA)) or for reaction of the product from IB) with formaldehyde, also plant parts for neutralization, washing, distillation and wastewater work-up.

The present invention therefore further provides a plant for preparing diamines and polyamines of the diphenylmethane series (MDA), which comprises the plant parts IA) a reactor having an integrated phase separation facility or a reactor and a separate phase separation apparatus for the reaction of aniline and formaldehyde in the absence of an acid catalyst to form an aminal and subsequently separation of the reaction mixture obtained into an aqueous phase and an organic phase containing the aminal and IIA) a reactor for reaction of the organic phase containing the aminal obtained in the reactor IA) with acid;

or

IB) a reactor for the reaction of aniline with acid and

IIB) a reactor for reaction of the reaction mixture obtained in the reactor IB) with formaldehyde;

and optionally

III) a reactor for neutralization of the reaction mixture from IIA) or IIB);

IV) a separation vessel for separation of the neutralized reaction mixture from III) into an organic phase comprising diamines and polyamines of the diphenylmethane series and an aqueous phase;

V) a washing vessel for washing of the organic phase from IV) by means of washing liquid;

VI) a separation vessel for separation of the mixture from V) into an organic phase comprising diamines and polyamines of the diphenylmethane series and an aqueous phase;

VII) a distillation apparatus for distillation of the organic phase from VI) to give diamines and/or polyamines of the diphenylmethane series and a stream containing water and aniline;

VIII) a wastewater work-up facility for work-up of the aqueous phase from IA) and/or the aqueous phase from IV) and/or the aqueous phase from VI) and/or the stream containing water and aniline from VII), preferably comprising a wastewater collection vessel, wastewater heater and aniline separation vessel, wherein the plant is configured in such a way that no further introduction of formaldehyde into the reactor IA) or IIB) takes place in the case of a shutdown of one or more of the plant parts I) to VIII), insofar as these are present, and the output stream can be recirculated in at least one of the plant parts which have not been shut down and used as feed stream for the respective plant part or an upstream plant part.

The plant of the invention preferably comprises the plant parts III) to VII), particularly preferably also plant part VIII).

For the purposes of the present invention, the configuration of the plant in such a way that "no further introduction of formaldehyde into the reactor IA) or IIB) takes place in the case of a shutdown of one or more of the plant parts I) to VIII), insofar as these are present" means that the introduction of formaldehyde is interrupted before or at the same time as the shutdown of a plant part, i.e. that the introduction of formaldehyde is interrupted before or at the same time as the setting of the circulatory mode of operation in at least one plant part which is not affected by the shutdown. In terms of apparatus, this can be achieved in various ways, for example by installation of process control facilities which automatically interrupt the introduction of formaldehyde when one or more plant parts are shut down (with setting of one or more of the plant parts which are not to be shut down to the circulatory mode of operation). The installation of a shut-off device which allows setting to the circulatory mode of operation only when the introduction of formaldehyde has been interrupted is likewise conceivable. Suitable software and hardware products are commercially available and known to those skilled in the art. Any necessary programming and adaptation work is a matter of routine for a person skilled in the art.

In a preferred embodiment of the present invention, the plant parts can be switched independently to feed streams consisting of recirculated output streams. In a further preferred embodiment, the plant parts can be switched simultaneously to feed streams consisting of recirculated output streams. Here, it is preferred that the output stream can be recirculated in any other, unaffected plant part and be used as feed stream for the respective plant part. When the plant comprises plant parts for washing the product stream (washing vessel V) and separation vessel VI), it is preferred that these plant parts are merely shut down in the case of interruption of the process but not set to the circulatory mode of operation.

The reactor IA) preferably comprises the aminal reactor, an aniline feed conduit to the reactor, a siphon and an aminal separator. The reactor IA) can further comprise an aminal cooler. The reactor IIB) preferably comprises a feed conduit which can be shut off for the reaction product of aniline and acid (or, if reactor IIB and IB are identical, in each case a separate feed conduit for aniline and acid), a feed conduit which can be shut off for formaldehyde, a mixing apparatus (preferably a stirrer) and a heat exchanger for regulating the temperature of the reaction mixture. The plant of the invention is preferably configured (particularly preferably by means of process control facilities) and operated in such a way that, when one or more plant parts other than the reactor IA) or the reactor IIB) are shut down, the formaldehyde stream into the reactor IA) or into the reactor IIB) is firstly stopped and then, preferably at least 10 minutes later, more preferably at least 20 minutes later and particularly preferably at least 30 minutes later, the aniline stream or the stream containing the reaction product of aniline and acid (or, if reactor IIB and IB are identical, the aniline stream and subsequently the acid stream) is stopped. In variant A), the aminal diluted with aniline is then pumped in uncooled form from the aminal reactor via the siphon into the aminal separator and from there circulated by pumping back via the aniline feed conduit to the aminal reactor for an indeterminate time or at least for the selected time. In variant B), the mixing apparatus is then switched off.

The reactor IIA) in which the acid-catalyzed rearrangement reaction takes place in variant A) preferably comprises a reactor cascade made up of a plurality of rearrangement reactors and residence towers, i.e., for example, a first rearrangement tank, an aminal conduit and a rearrangement cascade. The reactor IB) in which the reaction of aniline and acid takes place in variant B) preferably comprises an aniline feed conduit which can be shut off, an acid feed conduit which can be shut off, a mixing apparatus, particularly preferably a stirrer, and a heat exchanger for regulating the temperature of the reaction mixture. The plant of the invention is preferably configured (particularly preferably by means of process control facilities) and operated so that, in the case of a shutdown of one or more plant parts other than the reactor IIA) or the reactor IB), the acid stream, preferably a hydrochloric acid stream, into the reactor IIA) or into the reactor IB) is firstly stopped and the aminal stream or the stream comprising aniline into the reactor IIA) or into the reactor IIB) is subsequently stopped. In variant A), the condensate solution which forms the output stream from the reactor IIA) and comprises crude MDA, aniline and hydrochlorides thereof is then circulated, preferably without heating, from the last rearrangement reactor to the first rearrangement reactor or optionally into the second, third, etc., rearrangement reactor and via the (remaining) reactor cascade and the aminal conduit for an indeterminate time or at least for the selected time. In variant B), the mixing apparatus (preferably a stirrer) is then preferably switched off. The conveying of the condensation solution in variant A is preferably carried out by means of pumps.

Furthermore, preference is given to the reactor for neutralization III) in the plant of the invention to comprise a base feed facility (preferably a sodium hydroxide feed facility), a neutralization stirred vessel and a neutralization condenser to condense the vapor formed. Furthermore, preference is given to the separation vessel IV) comprising a neutralization separator with circulation pump for the lower alkaline, aqueous phase. The plant of the invention is preferably configured (particularly preferably by means of process control facilities) and operated so that, when one or more plant parts other than the reactor III) and separation vessel IV) are shut down, the acid condensation solution is firstly stopped and then, preferably 5 minutes later, more preferably 10 minutes later and particularly preferably 15 minutes later, the inflow of the base (preferably sodium hydroxide solution or ammonia, particularly preferably sodium hydroxide solution) and the inflow of the washing water are stopped. Thus, the mixture present in the neutralization separator can be pumped for an indeterminate time by means of the circulation pump from the neutralization separator into the neutralization stirred vessel via a siphon back into the neutralization separator and this part of the plant or the process step can thus be operated in the circulation mode in this way.

The washing vessel V) of the plant of the invention preferably comprises a crude MDA washer and a washing water addition. The separation vessel VI) of the plant of the invention comprises a phase separation apparatus for separating the mixture formed in the washing vessel V) into an organic, MDA-containing phase and an aqueous phase. The plant of the invention is preferably configured (particularly preferably by means of process control facilities) and is preferably operated so that, when one or more plant parts other than the washing vessel V) and separation vessel VI) are shut down, the washing water addition, consisting of condensates and/or the side stream from the process wastewater column, is stopped and the mixture present in each case in the washing vessel V) and separation vessel VI) is allowed to stand. A circulatory mode of operation is preferably dispensed with in these plant parts.

The distillation apparatus VII) of the plant of the invention preferably comprises a distillation plant with vacuum system, comprising a pump reservoir of the distillation for the crude MDA containing aniline and water, a heat exchanger, a predistillation column with condensation system for removing excess aniline, water and low boilers, an MDA column with bottom offtake of the end product MDA and a steam generator. The plant of the invention is preferably configured and operated (particularly preferably by means of process control facilities) so that when one or more plant parts other than the distillation apparatus VII) are shut down, no more crude MDA is introduced into the pump reservoir of the distillation after the wash has been stopped. Preference is therefore given to the bottom outflow from the MDA column to be conveyed via the steam generator and the heat exchanger back into the pump reservoir of the distillation and this part of the plant thus being operated in the circulation mode via the pump reservoir, the heat exchanger, the predistillation column and in the bottom of the MDA column. The steam to the predistillation column and MDA column can then be shut off. The vacuum system of the two columns can subsequently be shut down. In this way, the circulatory mode of operation can be run for any length of time without heating and vacuum.

If the preceding plant parts are, according to the invention, set to the circulatory mode of operation, no more wastewater is obtained in the wastewater work-up VIII) which is preferably present. The wastewater work-up of the plant of the invention preferably comprises a wastewater collection vessel, wastewater heater and aniline separation vessel. The plant of the invention is preferably configured and preferably operated (particularly preferably by means of process control facilities) so that when one or more of the plant parts other than the wastewater work-up are shut down, the wastewater extraction is set to the circulatory mode of operation by conveying the outflow from the aniline separation vessel to the wastewater collection vessel and circulating it by means of one or more pumps via the process wastewater heater into the aniline separation vessel. This circulatory mode of operation can be run for any length of time without heating.

In addition, the plant of the invention or the process of the invention can additionally comprise a wastewater distillation which can comprise a heat exchanger, a process wastewater distillation column with condensation system, a process wastewater cooler and a side stream receiver of the process wastewater distillation column. The wastewater distillation can, according to the invention, be stopped in the case of an interruption of the MDA production process, for example simply by shutting off the steam to the column. A circulatory mode of operation of the wastewater distillation can, but does not have to be, be carried out.

These preferred embodiments are naturally only examples of many possible circulatory modes of operation whose precise configuration depends on the specific circumstances of a production plant, but can be easily adapted to the specific circumstances within the scope of the present invention. However, a feature common to all conceivable circulatory modes of operation is that no product leaves the plant when the plant is a single-stream MDA line.

If two or more MDA reactor lines are to be operated in parallel, then product can, but does not have to, leave the plant, for example when the plant is operated at partial load.

The present invention further provides a method of operating a plant for preparing diamines and polyamines of the diphenylmethane series (MDA), which comprises the following plant parts:

IA) a reactor having an integrated phase separation facility or a reactor and a separate phase separation apparatus for the reaction of aniline and formaldehyde in the absence of an acid catalyst to form an aminal and subsequently separation of the reaction mixture obtained into an aqueous phase and an organic phase containing the aminal and IIA) a reactor for reaction of the organic phase containing the aminal obtained in the reactor IA) with acid;

or

IB) a reactor for the reaction of aniline with acid and

IIB) a reactor for reaction of the reaction mixture obtained in the reactor IB) with formaldehyde;

and optionally

III) a reactor for neutralization of the reaction mixture from IIA) or IIB);

IV) a separation vessel for separation of the neutralized reaction mixture from III) into an organic phase comprising diamines and polyamines of the diphenylmethane series and an aqueous phase;

V) a washing vessel for washing of the organic phase from IV) by means of washing liquid;

VI) a separation vessel for separation of the mixture from V) into an organic phase comprising diamines and polyamines of the diphenylmethane series and an aqueous phase;

VII) a distillation apparatus for distillation of the organic phase from VI) to give diamines and/or polyamines of the diphenylmethane series and a stream containing water and aniline;

VIII) a wastewater work-up facility for work-up of the aqueous phase from IA) and/or the aqueous phase from IV) and/or the aqueous phase from VI) and/or the stream containing water and aniline from VII), preferably comprising a wastewater collection vessel, wastewater heater and aniline separation vessel, wherein, to shut down one or more plant parts I) to VIII), if these are present, the following steps are carried out:

(i) a) stopping of the introduction of formaldehyde into the reactor IA);

(ii) a) stopping of the introduction of aniline into the reactor IA);

(iii) a) stopping of the introduction of acid into the reactor IIA);
or
(i) b) stopping of the introduction of formaldehyde into the reactor IIB);
(ii) b) stopping of the introduction of acid into the reactor IB);
iii) b) stopping of the introduction of aniline into the reactor IB);
and
(iv) operation of at least one plant part in such a way that the output stream from the respective plant part is used as feed stream to the respective plant part or an upstream plant part;
(v) shutdown of at least one plant part;
(vi) optionally opening of the at least one plant part which has been shut down in step (v);
(vii) optionally performing of a maintenance, cleaning and/or repair measure in the at least one plant part which has been shut down in step (v);
(viii) optionally closing and optionally making inert of the at least one plant part which has been shut down in step (v).

Here, the plant of the method is preferably the plant according to the present invention. This method of the invention advantageously enables the plant to be operated in the circulatory mode of operation in the case of the above-described interruptions (shutdown of individual plant parts) and the advantages and effects according to the invention thus to be achieved. It is very particularly advantageous and therefore preferred to bring preferably all possible plant parts which can be switched to the circulatory mode of operation and are not affected in any way by the production stoppage into the circulatory mode of operation in step (iv), with the washing vessel V) and the separation vessel VI) particularly preferably being excepted from the circulatory mode of operation.

In a preferred embodiment, the method comprises the further steps
(ix) start-up of the at least one plant part which has been shut down in step (v),
(x) commencement of the introduction of formaldehyde into the reactor IA) or IIB) and commencement of the introduction of aniline into the reactor IA) or IB) and introduction of acid into the reactor IIA) or IB).

In a further preferred embodiment, which is particularly advantageous when there is only a shortage of raw material but no maintenance work waiting to be done, all plant parts, preferably with the exception of the washing vessel V) and the separation vessel VI), which are preferably stopped, as described above, are operated in step (iv) in such a way that the output stream from the respective plant part is used as feed stream to the respective plant part, and the method comprises, as an alternative to steps (v) to (x), the following steps:
xi) waiting for starting materials or auxiliaries and, as soon as these have arrived,
(xii) commencement of the introduction of formaldehyde into the reactor IA) or IIB) and commencement of the introduction of aniline into the reactor IA) or IB) and introduction of acid into the reactor IIA) or IB).

In the following, the setting of the plant to the circulatory mode of operation is described by way of example for the variant A) and the restarting of the plant from the circulatory mode of operation to normal operation is described, likewise by way of example:

In the first step, the introduction of formaldehyde into the aminal reactor is stopped. For a certain period of time, aniline is still introduced in order to dilute the reaction solution in the aminal reactor. Aniline is then turned off and the aminal region is set to the circulatory mode of operation.

In the second step, the rearrangement reactors are, after hydrochloric acid and aminal have been shut off, set to the circulatory mode of operation.

In the third step, the neutralization and washing are operated with circulation and the MDA still present in the distillation is diluted with aniline and the distillation is subsequently set to the circulatory mode of operation.

The plant part which is affected, for example, by a maintenance measure is emptied, cleaned and optionally opened for the measure to be carried out. The maintenance measure is then carried out and the plant part is closed again, optionally made inert and filled with auxiliaries and starting materials and prepared for start-up.

The restarting of the plant from the circulatory mode of operation can thus be carried out, for example, as follows:

In order to start the plant up again, the procedure is reversed. Since the vessels and apparatuses are very full with diluted production solution, firstly the distillation, then the neutralization and washing, subsequently the rearrangement reaction and at the end the aminal reaction are started up again. The wastewater work-up is commenced as soon as the neutralization is running.

Firstly, in the distillation with vacuum system, comprising a pump reservoir of the distillation for the crude MDA containing aniline and water, a heat exchanger, a predistillation column with condensation system for removing excess aniline, water and low boilers, MDA column with bottom offtake for the end product MDA and a steam generator, the vacuum system of the predistillation column and MDA column is firstly taken into operation for carrying out a start-up after the shutdown. The steam to the predistillation column and MDA column is then opened and the columns are heated up. The operating segment of distillation is then ready to accept crude MDA.

Separately, in the neutralization, comprising sodium hydroxide feed facility, neutralization stirred vessel, neutralization condenser for condensing the vapor formed, neutralization separator with circulation pump for the lower alkaline, aqueous phase, firstly the sodium hydroxide solution and the washing water and 10 minutes later the acidic condensation solution are turned on. The operating segment of neutralization has then been turned on, and crude MDA goes to washing.

Subsequently, in washing, comprising MDA washer, phase separation apparatus and washing water addition, the addition of washing water comprising condensate and/or the side stream from the process wastewater column is turned on. The operating segment of washing is then running, and crude MDA is fed to the distillation.

As soon as neutralization and washing are running process water once again goes into the wastewater work-up, comprising a wastewater extraction and a wastewater distillation, after shutting-down of the abovementioned plant parts. In order to extract traces of MDA from the process wastewater by means of aniline in the wastewater extraction, the wastewater extraction, which consists of a wastewater collection vessel, wastewater heater and aniline separation vessel, is started. For this purpose, the wastewater which is obtained from the above-described process steps (neutralization, washing and distillation) and arrives in the wastewater collection vessel is conveyed by means of a pump via the process wastewater heater into the aniline separation vessel. From there, the extracted wastewater goes to the wastewater distillation. The wastewater distillation, comprising a heat exchanger, a process wastewater distillation column with condensation system, a process wastewater cooler and a side stream receiver of the process wastewater distillation column, is then started up by opening the steam to the column and purified process wastewater leaves the production plant.

The aminal stream is subsequently turned on in the rearrangement reaction, comprising a reactor cascade made up of a plurality of rearrangement reactors and residence towers, and the HCl stream is subsequently started up. The condensation solution comprising MDA, aniline and hydrochloric acid is heated. The operating segment of the rearrangement reaction is then operational, and crude MDA goes to the neutralization.

Subsequently, firstly the aniline stream and then the formalin stream are turned on while stirring in the aminal reaction, comprising aminal reactor, aminal cooler and aminal separator. The aminal cooler is started up and the aminal solution is conveyed from the aminal reactor via the aminal cooler and then goes in cooled form from the aminal reactor via the siphon into the aminal separator. From there, the organic phase comprising aminal solution goes into the first reactor of the rearrangement reaction. The aminal water obtained in the aminal separator is fed to the wastewater work-up. The operating segment of the aminal reaction is then operational, and aminal solution goes to the rearrangement reaction.

The complete MDA plant is now running, preferably at a reduced load (start-up load), and can now be run up to the desired production throughput. Particular preference is given here to starting up the production plant at a reduced load since otherwise the required temperature profiles for aminal and rearrangement reaction, neutralization, washing and wastewater work-up and distillation are not able to be established quickly enough, which would lead to incomplete reactions, increased by-products and defective work-up of the product.

In the plants of the invention and the process and method according to the invention, each plant part can, for example, be set manually to the circulatory mode of operation. In a preferred embodiment, the switching over to the circulatory mode of operation, the start-up and the monitoring of all steps are carried out by means of a central control unit which particularly preferably comprises process control facilities.

The success of the procedure according to the invention is surprising to a person skilled in the art because such a person would, in order to be able to save energy in principle and concentrate on the maintenance measures to be carried out during the production stoppage, tend instead to shut down the total plant, especially when additional capital costs for recirculating pipes together with pumps, modifications on the apparatuses and additional process control technology are taken into account for the process of the invention or for the plant according to the invention.

The present invention is illustrated below by means of further examples.

EXAMPLES

General Conditions for the Preparation of MDA in a "Run-In" Production Plant (FIG. 1)

In a continuous reaction process (step a), 24.3 t/h of the aniline (stream 1, containing 90% by mass of aniline) and 9.9 t/h of 32% strength aqueous formalin solution (formaldehyde, stream 2) (molar ratio of aniline to formaldehyde 2.1:1) are mixed and reacted at 90° C. and 1.4 bar (absolute) in a stirred reaction vessel (1000) to form aminal. The reaction vessel is provided with a cooler having a cooling circulation pump. The reaction mixture (4) leaving the reaction vessel is conveyed into a phase separation apparatus (aminal separator, 2000) (step b). After phase separation to remove the aqueous phase (5), which is fed into a wastewater collection vessel (not shown), the organic phase (6) is admixed in a mixing nozzle with 30% strength aqueous hydrochloric acid (3) (degree of protonation 10%, i.e. 0.1 mol of HCl are added per mole of amino groups) and fed into the first rearrangement reactor. The rearrangement reaction is carried out in a reactor cascade (3000) at from 45° C. to 165° C. (step c). After the reaction is complete, the reaction mixture (7) obtained is admixed with 32% strength sodium hydroxide solution (8) in a molar ratio of sodium hydroxide to HO of 1.1:1 and reacted in a neutralization stirred vessel (4000) (step d)). The temperature here is 115° C. and the absolute pressure is 1.4 bar. The neutralized reaction mixture (9) is subsequently separated in a neutralization separator (5000) into an aqueous, lower phase (10), which is fed into a wastewater collection vessel (not shown), and an organic phase (11) (step e). The Organic, upper phase is conveyed to washing and washed in a stirred washing vessel (6000) with condensate and/or water from the side stream from the wastewater column (aniline/water mixture) (11) (step f). After the washing water (14) has been separated off in a washing water separator (7000, step g)), the crude MDA (13) obtained in this way is freed of water and aniline (15) by distillation in the distillation apparatus (8000), giving 17 t/h of MDA (16) as bottom product (step h). The washing water (14) is fed into a wastewater collection vessel (not shown).

Example 1 (Comparative Example)

Running-Down of the Plant to a Complete Stop for a Repair and Renewed Start-Up of the Plant Firstly, the entire production plant of example 1 was brought to a production load of 10 t/h of MDA in order to be able to flush the plant very quickly with aniline but produce very little waste product such as aniline, crude MDA and wastewater, all of which have to be treated again.

The shutdown of the plant was commenced by turning off the feed stream of formaldehyde into the aminal reactor. For this purpose, the formaldehyde pump was stopped and the formaldehyde conduit from the formaldehyde stock tank was flushed free of formaldehyde by means of water for 10 minutes. The aminal part of the plant was then diluted with aniline for 3 hours, with residual formaldehyde reacting to form aminal and being flushed out of the aminal reactor. During the flushing procedure, the amount of aniline was increased in such a way that compensation for the now missing amount of aniline took place in order to ensure a constant mass flow and not to have to reduce the levels in the subsequent apparatuses. Heat of reaction was no longer involved after stopping of the introduction of formalin and the aminal reactor cooled to 67° C. After 3 hours, the introduction of aniline was stopped, the cooling circuit was shut down and the aminal cooler, the aminal pump and the aminal stirred vessel were completely emptied in succession into the aminal separator. The pressure in the aminal vessel remained at 1.4 bar absolute during the flushing procedure. The aminal separator was then likewise emptied completely by the flushing aniline and the residual water located above the aniline being conveyed into the first rearrangement reactor. The aminal part was then at a standstill. The running-down of the aminal region had taken a total of 5 hours.

Next, the reactor cascade of the rearrangement reaction was run down. Here, the reactor cascade was no longer supplied with steam as early as 2 hours after commencement of the shutdown of the aminal part of the plant in order to compensate for the heat of reaction which was no longer produced. The temperatures in the reactor cascade were left at from 45° C. to 165° C. The running-down of the reactor cascade was commenced by stopping the introduction of the 30% strength aqueous hydrochloric acid into the mixing nozzle upstream of the first rearrangement reactor at the point of time when the complete emptying of the aminal separator was started. The reactors of the reactor cascade were then emptied in succession into the neutralization. Steam and vacuum were stopped when the last rearrangement tank was empty. The reactor cascade of the rearrangement reaction was now at a standstill. The running-down of the reactor cascade had taken a total of 3 hours.

The neutralization was then shut down by feeding further 32% sodium hydroxide solution into the neutralization stirred vessel for 10 minutes longer than diluted reaction mixture from the reactor cascade of the rearrangement reaction. The contents of the neutralization stirred vessel and separator were then completely emptied into an alkaline drainage vessel.

The absolute pressure remained at 1.4 bar. The neutralization was then at a standstill. The running-down pressures with complete emptying had taken 2 hours.

Next, the washing was shut down by firstly shutting off condensate and/or water from the side stream of the wastewater column (aniline/water mixture) to the stirred washing vessel. The stirrer of the washing vessel was switched off and the contents of the washing vessel were emptied into the washing water separator. The contents of the washing water separator were emptied into the distillation reservoir. Washing was then at a standstill. The running-down procedure had taken 2 hours.

Finally, the distillation was shut down by setting the complete distillation to the circulatory mode of operation after the washing part has been completely emptied; the crude MDA present in the distillation was diluted with 6 t/h of aniline from the aniline stock tank. The steam to the distillation was shut off. The distillation was run down to cold over a period of 4 hours with the vacuum still prevailing. Subsequently, the vacuum was shut off and the contents of the complete distillation (distillation reservoir, heat exchanger, predistillation column with condensation system, MDA column with bottom offtake, steam generator) were emptied into the alkaline drainage vessel. The distillation was then at a standstill, with the running-down procedure having taken 4 hours.

While the distillation was being run down to cold, the wastewater work-up was shut down by firstly emptying the aniline/water mixture from the wastewater extraction, which consisted of wastewater collection vessel, wastewater heater and aniline separation vessel, into the wastewater tank. The wastewater distillation, consisting of a heat exchanger, a process wastewater distillation column with condensation system, a process wastewater cooler and a side stream reservoir of the process wastewater distillation column, was shut down by shutting off the steam to the wastewater distillation and subsequently emptying the contents of the wastewater distillation into the wastewater tank.

The complete MDA plant had now been completely emptied at this point in time and was at a standstill. The plant pressure was set to ambient pressure by all pressure maintenance devices of the plant being turned off. The complete emptying facilities of all plant parts were opened again in order to drain residues from the plant. The complete shutdown with emptying of all apparatuses, pumps and pipes had taken a total of 24 hours.

Consumption: 20 standard $m^3$ of nitrogen were consumed for breaking the vacuum and 500 kW of power had been consumed for the circulatory mode of operation of the distillation. Furthermore, there was an increased steam requirement in the reactor cascade of the rearrangement reaction of 5 metric tons of 6 bar steam and 5 metric tons of 16 bar steam. In addition, 10 metric tons of flushing aniline had arisen and this had to be treated before use in the aminal reaction.

Carrying Out a One-Day Maintenance Measure

A defective stirring device had to be replaced in the washing vessel.

Preparation for Restarting of the Plant

All plant parts were firstly brought into the circulatory mode of operation. The restarting of the plant commenced with the parallel start-up of all circuits of the total plant. The plant parts were firstly filled with aniline and/or auxiliaries such as HCl or NaOH.

Filling of the Aminal Part and Setting of the Circulatory Mode of Operation:

The aniline reservoir was firstly filled with fresh aniline from the aniline stock tank. The empty aminal reactor was then filled with aniline until aniline flowed over via the siphon into the aminal separator. When the aminal separator had been half-filled with aniline, the aniline stream to the aminal reactor was shut off and the aminal circulatory mode of operation was started by means of the pump from the aminal separator. 4 t/h of aniline were then circulated by pumping from the aminal separator via the aminal reactor. Time required: 3 hours.

Filling of the Reactor Cascade of the Rearrangement Reaction and Setting of the Circulatory Mode of Operation:

The first rearrangement reactor was filled to a level of 60% with fresh aniline from the aniline stock tank. The aniline stream was then shut off and the contents of the first rearrangement reactor were circulated together with 24 t/h of fresh aniline by means of the discharge pump. The remaining rearrangement reactors of the reactor cascade were filled with a mixture consisting of aniline, hydrochloric acid and traces of crude MDA from the acidic drainage vessel and the rearrangement circulatory mode of operation was started by means of the pumps of the rearrangement reactors from the last rearrangement reactor to the second rearrangement reactor. 10 t/h of the mixture from the acidic drainage vessel were then circulated by pumping and heated to 100° C. by means of steam. The remaining 15 metric tons of the mixture from the acidic drainage vessel had to be mixed in later during ongoing production, although this means a fluctuation in the 2-ring content of the end product. Time required: 8 hours.

Filling of the Neutralization and Setting of the Circulatory Mode of Operation 2 metric tons of 32% strength sodium hydroxide solution from the sodium hydroxide stock tank and 8 metric tons of condensate from the condensate stock vessel were fed into the neutralization stirred vessel. The neutralization stirred vessel was then full and 2 metric tons of the diluted sodium hydroxide solution had flowed over via the siphon into the neutralization separator. The circulatory mode of operation was started by means of the pump of the neutralization separator by pumping the diluted sodium hydroxide from the neutralization separator into the neutralization stirred vessel. 4 t/h of diluted sodium hydroxide solution were then circulated by pumping from the neutralization separator via the neutralization stirred vessel. Time required: 4 hours.

The Washing Facility was Not Filled and Also Not Set to the Circulatory Mode of Operation:

The stirred vessel of the washing facility and the separator connected thereto remain empty until start-up of the plant.

Filling of the Distillation and Setting of the Circulatory Mode of Operation

The distillation reservoir was filled to a level of 60% with fresh aniline from the aniline stock tank. The complete distillation consisting of heat exchanger, predistillation column with condensation system, MDA column with bottom offtake and steam generator were then filled with fresh aniline from the distillation reservoir, fresh aniline was shut off and 10 t/h of fresh aniline were circulated via the predistillation column and MDA column. The vacuum of the distillation was then started up and the entire distillation was heated to 100° C. by means of steam. Time required: 5 hours.

Filling of the Wastewater Work-Up and Setting of the Circulatory Mode of Operation:

Wastewater was pumped from the wastewater tank into the wastewater collection vessel. Wastewater was then conveyed from the wastewater collection vessel into the wastewater heater and aniline separation vessel. Fresh aniline from the aniline stock tank was then fed to the wastewater heater, the wastewater heater was subsequently heated to 90° C. and the mixture of fresh aniline and wastewater was circulated from the wastewater heater via the aniline separation vessel and the wastewater collection vessel. The wastewater distillation remained shut down until start-up of the plant. Time required: 5 hours.

A total of 15 hours were required to bring the total plant, as described, into the circulatory mode of operation because parts of the plant were filled in parallel. This required 50 metric tons of 16 bar steam and 9500 kW of power for operation of the motors.

Restarting of the Plant

The plant ran, as described in the preparations for restarting of the plant, in the circulatory mode in the individual operating segments, i.e. it had been heated up, stirrers were in operation, blanketing pressure of nitrogen and vacuum prevailed in the necessary regions. Starting materials and auxiliaries were ready.

Start-Up of the Distillation with Vacuum System:

The distillation with vacuum system was in the circulatory mode of operation. The vacuum system of the predistillation column and the MDA column was started up and set to 120 mbar absolute. The 16 bar steam (consumption: 40 metric tons) to the predistillation column and the 110 bar steam (consumption: 10 metric tons) to the MDA column were then opened and the columns were heated up. The temperature in the predistillation column was 190° C. and that in the MDA column was 225° C. The aniline required for distillation was fed from the aniline reservoir into the pump reservoir of the distillation during the time of circulatory operation. The steam generator was in operation. The operating segment of distillation was then ready for receiving crude MDA. Time required: 3 hours.

Start-Up of the Aminal Reaction:

30 minutes before the distillation was ready to receive crude MDA, the aminal production was started by opening the aniline supply to the aminal reactor and staring the formalin stream 10 minutes later. At the same time, the conduit for the organic phase having a temperature of 90° C.

from the aminal separator to the first reactor of the rearrangement reaction was opened and the temperature in the first rearrangement reaction was reduced to 50° C. by means of vacuum. The acid catalysis of the rearrangement reaction by means of hydrochloric acid could now be started. The aminal water obtained in the aminal separator was fed to the wastewater work-up. The operating segment of the aminal reaction was now operational and aminal solution went to the rearrangement reaction. Time required: 15 minutes.

Start-Up of the Rearrangement Reaction:

After the hydrochloric acid stream had been started up and the temperature in the first rearrangement reactor had been established, the further rearrangement reactors and residence towers of the reactor cascade were heated to 60° C. up to the last reactor to 165° C. (consumption: 60 metric tons of 16 bar steam). The operating segment of the rearrangement reaction was now operational and the condensation solution consisting of MDA, aniline and hydrochloric acid (crude MDA) was next neutralized. Time required: 10 minutes.

Start-Up of the Neutralization:

The sodium hydroxide feed facility was started up by feeding sodium hydroxide solution and washing water into the neutralization stirred vessel. 10 minutes later, the conduit for the acidic condensation solution from the rearrangement reaction was opened. The operating segment of neutralization was now operational and the neutralized crude MDA could be washed. Time required: 10 minutes.

Start-Up of Washing:

Neutralized crude MDA having a temperature of 116° C. arrived in the MDA washer and was washed by means of condensate. The washing water addition, consisting of condensate and/or the side stream from the process wastewater column, was started up. The operating segment of washing was then operational. Neutralized and washed crude MDA left the phase separation apparatus and went to the distillation. Time required: 5 minutes.

Start-Up of the Wastewater Work-Up:

As soon as the neutralization and washing were running, the wastewater work-up was started up by starting the wastewater extraction and the wastewater distillation. For this purpose, the wastewater which had been obtained from the above-described process steps (neutralization, washing and distillation) and arrived in the wastewater collection vessel was conveyed by means of a pump via the process wastewater heater into the aniline separation vessel. From there, the extracted wastewater went to the wastewater distillation. The wastewater distillation was heated to 107° C. by means of 20 metric tons of 6 bar steam, and the wastewater left the production plant. Time required: 2 hours.

The complete MDA plant was now running at a reduced load of 10 t/h of MDA and could then be run up to the desired production throughput. A total of 10 hours were required in order to start up the total plant, as described, from the circulatory mode of operation and discharge the first end product into the MDA tank. 100 metric tons of 16 bar steam, 10 metric tons of 110 bar steam and 20 metric tons of 6 bar steam and also 6315 kW power for operating the motors were required for this purpose.

It was absolutely necessary to start up the production plant at a reduced load since otherwise the temperature profiles required for aminal and rearrangement reaction, neutralization, washing and wastewater work-up and distillation were not established quickly enough. This would lead to incomplete reactions, increased by-products and defective work-up of the product.

Conclusion:

The time required for the overall production stoppage (running-down, measure and start-up) was 73 hours.

The energy consumption for this (running-down, measure and start-up) was 15 815 kW of power, 105 metric tons of 16 bar steam, 10 metric tons of 110 bar steam and 25 metric tons of 6 bar steam. In addition, auxiliaries in the form of 20 standard $m^3$ of nitrogen were consumed for breaking the vacuum.

Example 2 (According to the Invention)

Bringing the Plant into the Circulatory Mode of Operation, Repair in the Washing Facility, Restarting of the Plant from the Circulatory Mode of Operation Firstly, the total production plant was brought to the optimal production load of 10 t/h of MDA as described in comparative example 1 in order then to bring the entire plant into the circulatory mode of operation.

Figure 2:
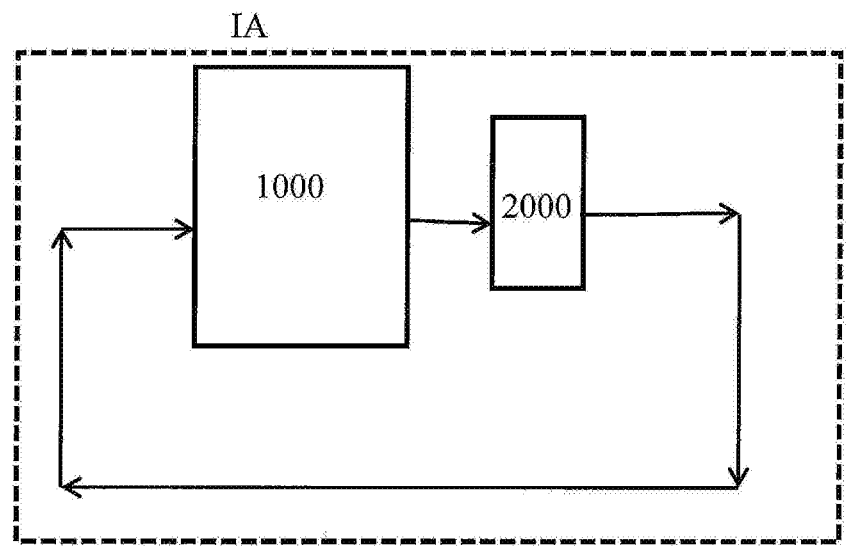
FIG. 2 is a flow diagram illustrating a circulatory mode of operation of the aminal part of the plant in Example 2.

The actual setting of the plant to the circulatory mode of operation commenced with shutting off the feed stream of formaldehyde into the aminal reactor. For this purpose, the formaldehyde pump was stopped, and the formaldehyde conduit from the formaldehyde stock tank was washed free of formaldehyde by means of water for 10 minutes. The aminal part of the plant was then diluted with aniline for 30 minutes, with formaldehyde continuing to react to form aminal and the aminal solution being diluted. During the flushing procedure, the amount of aniline was increased so that compensation for the now missing amount of aminal took place in order to ensure a constant mass flow and not to have to reduce the levels in the downstream apparatuses. The heat of reaction was no longer produced after the introduction of formaldehyde had been stopped and the aminal reactor cooled to 67° C. After 30 minutes, the introduction of aniline was stopped and the aminal part of the plant was set to the circulatory mode of operation by pumping the aminal diluted with aniline in uncooled form from the aminal reactor via the siphon into the aminal separator and from there circulating it back to the aminal reactor (FIG. 2). The pressure in the aminal vessel remained at 1.4 bar absolute during the circulatory mode of operation. Setting of the aminal part of the plant to the circulatory mode of operation took a total of 1 hour.

Next, the reactor cascade of the rearrangement reaction was brought into the circulatory mode of operation by firstly shutting off the hydrochloric acid stream and then the aminal stream. The condensation solution consisting of MDA, aniline and hydrochloric acid could then be circulated by pumping, without heating, from the last rearrangement reactor to the first rearrangement reactor and via the reactor cascade. The setting of the rearrangement part of the plant to the circulatory mode of operation took a total of 1 hour.

Figure 3:
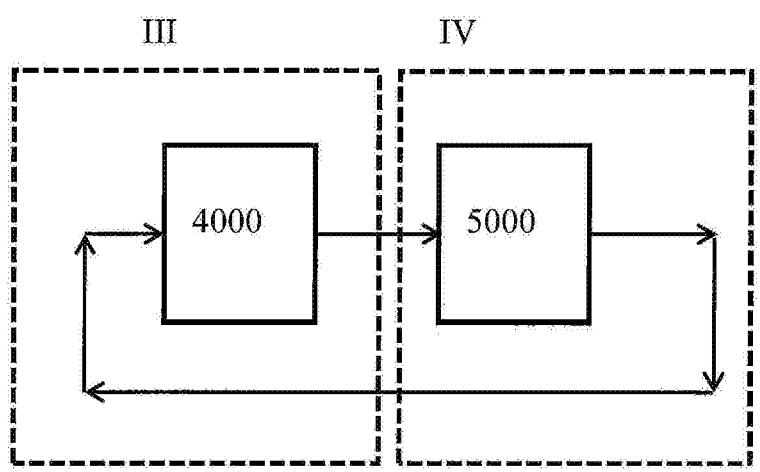
FIG. 3 is a flow diagram illustrating a circulatory mode of operation of the neutralization part of the plant in Example 2.

Next, the neutralization was set to the circulatory mode of operation by firstly shutting off the acidic condensation solution coming from the rearrangement reaction and 10 minutes later shutting off the 32% strength sodium hydroxide solution and the washing water. The contents of the neutralization separator were then pumped by means of the circulating pump from the neutralization separator into the neutralization stirred vessel and via the siphon back into the neutralization separator. The circulatory mode of operation (FIG. 3) had thus been established. The pressure in the neutralization remained at 1.4 bar absolute. Setting of the neutralization part of the plant to the circulatory mode of operation took a total of 40 minutes.

Next, the washing facility was shut down by closing off the washing water addition, consisting of condensate, to the stirred washing vessel. The stirrer of the washing vessel was stopped. In order to prepare for the repair measure in the washing facility, the contents of the washing vessel were emptied into the washing water separator. The contents of the washing water separator were emptied into the distillation reservoir. The washing facility was now at a standstill. This running-down procedure took 2 hours.

Lastly, the distillation was set to the circulatory mode of operation by, after the washing facility had been completely emptied, diluting the crude MDA present in the distillation with 6 t/h of aniline from the aniline stock tank. No more crude MDA arrived in the pump reservoir of the distillation. The outflow from the bottom of the MDA column was sent via the steam generator and the heat exchanger back to the pump reservoir of the distillation and thus circulated via the pump reservoir, the heat exchanger, the predistillation column and back into the bottom of the MDA column. The steam to the predistillation column and MDA column could now be shut off The vacuum system of the two columns could subsequently be shut off. The setting of the distillation part of the plant to the circulatory mode of operation took a total of 3 hours.

Finally, the wastewater work-up was brought to the circulatory mode of operation when no more process water was obtained. The wastewater extraction, consisting of wastewater collection vessel, wastewater heater and aniline separation vessel, was set to the circulatory mode of operation by switching the outflow from the aniline separation vessel to the wastewater collection vessel and circulating it by means of a pump via the process wastewater heater into the aniline separation vessel. The circulatory mode of operation could be operated for an indeterminate time without heating. The wastewater distillation, consisting of a heat exchanger, a process wastewater distillation column with condensation system, a process wastewater cooler and a side stream reservoir of the process wastewater distillation column, was shut down by shutting off the steam to the column. A circulatory mode of operation of the wastewater distillation was not provided here.

The complete MDA plant except for washing was now running in the circulatory mode of operation. Setting of the circulatory mode of operation had taken 6 hours.

Consumption: 20 standard $m^3$ of nitrogen for breaking the vacuum and 3825 kW of power in order to bring the plant to the circulatory mode of operation, generation of 10 metric tons of flushing aniline in the distillation, which had to be treated before use in the aminal reaction.

Carrying Out a One-Day Maintenance Measure

A defective sight glass and a leaking seal had to be replaced on the washing vessel. 15 300 kW of power were required for the circulatory mode of operation during the measure. Only a little steam was consumed for keeping the circuit at temperature (12 metric tons of 16 bar steam).

Preparation for Restarting the Plant

The preparations for restarting the plant were dispensed with since all plant parts were already running in the circulatory mode of operation. The filling of the plant parts with aniline and/or auxiliaries such as hydrochloric acid or sodium hydroxide solution therefore also did not need to be carried out.

Restarting of the Plant

The plant was, as described above, in the preparations for restarting of the plant, running in the circulatory mode in the individual operating segments. Starting materials and auxiliaries were available, the plant parts had been heated up, stirrers were in operation, blanketing pressure of nitrogen prevailed in the required regions and vacuum likewise prevailed.

The restarting of the plant was carried out as described in example 1 (comparative example). The complete MDA plant now ran at a reduced load of 10 t/h of MDA and could then be run up to the desired production throughput. A total of 10 hours were again required in order to bring the total plant, as described, from the circulatory mode of operation into the production mode and discharge the first end product into the MDA tank.

This likewise required 100 metric tons of 16 bar steam, 10 metric tons of 110 bar steam and 20 metric tons of 6 bar steam and also 6315 kW of power for operating the motors.

The time taken for the total action (running-down, measure and start-up) was 40 hours. There was thus an additional production of 522.5 metric tons of MDA compared to example 1 (comparative example) at a nominal load of 380 metric tons per day.

The energy consumption for the total action (running-down, measure and start-up) was 25 500 kW of power, 112 metric tons of 16 bar steam, 10 metric tons of 110 bar steam and 25 metric tons of 6 bar steam and also a consumption of auxiliaries in the form of 20 standard m³ of nitrogen for breaking the vacuum.

Conclusion: An additional 7 metric tons of 16 bar steam and 9685 kW of power were consumed in example 2 according to the invention with circulatory mode of operation than in a complete shutdown of the plant as in example 1 (comparative example). However, this was compensated for by greatly improved productivity of the plant since over 500 metric tons more of MDA could be produced because of the shorter time requirement for the total action (running-down, measure and start-up).

The invention claimed is:

1. A plant for preparing diamines and polyamines of the diphenylmethane series, which comprises the plant parts:
   IA) a reactor having an integrated phase separation facility or a reactor and a separate phase separation apparatus configured to react aniline and formaldehyde in the absence of an acid catalyst to form an aminal and configured to subsequently separate the reaction mixture obtained into an aqueous phase and an organic phase containing the aminal; and
   IIA) a reactor configured to react the organic phase containing the aminal obtained in the reactor IA) with acid;
   or
   IB) a reactor configured to react aniline with acid; and
   IIB) a reactor configured to react the reaction mixture obtained in the reactor IB) with formaldehyde;
   and
   III) a reactor configured to neutralize the reaction mixture from IIA) or IIB);
   IV) a separation vessel configured to separate the neutralized reaction mixture from III) into an organic phase comprising diamines and polyamines of the diphenylmethane series and an aqueous phase;
   V) a washing vessel configured to wash the organic phase from IV) by means of washing liquid;
   VI) a separation vessel configured to separate the mixture from V) into an organic phase comprising diamines and polyamines of the diphenylmethane series and an aqueous phase;
   VII) a distillation apparatus configured to distill the organic phase from VI) to give diamines and polyamines of the diphenylmethane series and a stream containing water and aniline; and optionally
   VIII) a wastewater work-up facility configured to work-up the aqueous phase from IA) and/or the aqueous phase from IV) and/or the aqueous phase from VI) and/or the stream containing water and aniline from VII);
   wherein
   the plant is configured such that during a shutdown of one or more, but not all, plant parts, the shutdown involving a complete stoppage of the plant part:
      introduction of formaldehyde into the reactor IA) or IIB) is interrupted before or at the same time as the shutdown; and
      an output stream from at least one of the plant parts which is not shut down is recirculated and the output stream is used as a feed stream for the respective plant part or an upstream plant part.

2. The plant as claimed in claim 1, wherein a process control facility is configured to interrupt introduction of formaldehyde into reactor IA) or IIB) before or at the same time as the shutdown of the one or more plant parts.

3. The plant as claimed in claim 1, wherein the plant is configured to recirculate and use as a feed stream to the respective plant part the output stream in each plant part which has not been shut down, with the exception of the washing vessel V) and the separation vessel VI), insofar as these are present.

4. The plant as claimed in claim 1, wherein the plant is configured to simultaneously recirculate and use as a feed stream the output streams in all plant parts which have not been shut down.

5. The plant as claimed in claim 1, wherein the plant is configured to independently recirculate and use as a feed stream the output streams in all plant parts which have not been shut down.

6. The plant as claimed in claim 1, wherein reactor IA) comprises an aniline feed conduit to the reactor, a siphon and a phase separator configured to separate off aniline, where reactor IA) is configured to circulate aniline via the aniline feed conduit, the siphon and the phase separator and back to the aniline feed conduit,
   or
   reactor IB) comprises an aniline feed conduit configured to be shut off, an acid feed conduit configured to be shut off, a mixing apparatus and a heat exchanger configured to regulate the temperature of the reaction mixture, where the mixing apparatus in the reactor IB) is configured to shut down after the aniline feed conduit and the acid feed conduit are shut off.

7. The plant as claimed in claim 1, wherein the reactor IIA) comprises a rearrangement tank, an aminal conduit and a rearrangement cascade, wherein the reactor IIA) is configured to circulate the output stream via the aminal conduit into the rearrangement tank, the rearrangement cascade and the aminal conduit into the rearrangement tank,
   or
   reactor IIB) comprises a feed conduit for the reaction product of aniline and acid which is configured to be shut off or, if reactor IIB) and IB) are identical, in each case a separate feed conduit for aniline and acid, a feed conduit for formaldehyde configured to be shut off, a mixing apparatus and a heat exchanger configured to regulate the temperature of the reaction mixture, where the mixing apparatus in the reactor IIB) is configured to be shut down after the feed conduit for formaldehyde is shut off and after the feed conduit for the reaction product of aniline and acid is shut off, or, if reactor IIB) and IB) are identical, after the feed conduit for aniline and the feed conduit for acid is shut off.

8. A process for preparing diamines and polyamines of the diphenylmethane series using the plant of claim 1, which comprises the steps:

IA) reacting aniline and formaldehyde in the absence of an acid catalyst in the reactor of plant part IA) to form an aminal, with aniline being introduced at a mass flow rate $m_1$ and formaldehyde being introduced at a mass flow rate $m_2$ into the reactor, followed by separation of the reaction mixture obtained into an aqueous phase and an organic phase containing the aminal in the phase separation facility integrated into the reactor or in the separate phase separation apparatus; and IIA) reacting at least part of the organic phase containing the aminal which is obtained in step IA) with acid in the reactor of plant part IIA), with the aminal reacting to form diamines and/or polyamines of the diphenylmethane series;

or

IB) reacting aniline and acid in the reactor of plant part IB); and

IIB) reacting at least part of the reaction mixture obtained in step IB) with formaldehyde in the reactor of plant part IIB) to form diamines and polyamines of the diphenylmethane series, with the aniline-containing reaction mixture from step IB) being introduced at a mass flow rate $m_1$ and formaldehyde being introduced at a mass flow rate $m_2$ into the reactor of step IIB);

and the optional steps III) to VIII) III) neutralizing the reaction mixture obtained in step IIA) or IIB) in the reactor of plant part III);

IV) separating the neutralized reaction mixture obtained in step III) into an organic phase comprising diamines and polyamines of the diphenylmethane series and an aqueous phase in the separation vessel of plant part IV);

V) washing the organic phase with washing liquid in the washing vessel of plant part V);

VI) separating the mixture obtained in step V) into an organic phase comprising diamines and polyamines of the diphenylmethane series and an aqueous phase in the separation vessel of plant part VI);

VII) distilling the organic phase from step VI) in the distillation apparatus of plant part VII), with diamines and polyamines of the diphenylmethane series being separated off from water and aniline, giving a stream containing water and aniline; and VIII) working up the aqueous phase from step IA) and/or the aqueous phase from step IV) and/or the aqueous phase from step VI) and/or the stream containing water and aniline from step VII) in the wastewater work-up facility of plant part VIII);

wherein in the case of a shutdown of one or more plant parts of steps I) to VIII), if these are carried out, the mass flow rate $m_2$ in step IA) or in step IIB) is reduced to zero and the output stream from at least one of the plant parts which have not been shut down is reused as feed stream to the respective plant part or an upstream plant part.

9. The process as claimed in claim 8 comprising the steps III) to VII).

10. The process as claimed in claim 8, wherein the output stream in all plant parts which have not been shut down, with the exception of the washing vessel used in step V) and the separation vessel used in step VI), is reused as feed stream to the respective plant part.

11. A method of shutting down one or more plant parts I) to VIII) in the plant of claim 1, comprising:

(i) a) stopping the Introduction of formaldehyde into the reactor IA);

(ii) a) stopping the introduction of aniline into the reactor IA);

(iii) a) stopping the introduction of acid into the reactor IIA);

or (i) b) stopping the introduction of formaldehyde into the reactor IIB);

(ii) b) stopping the introduction of acid into the reactor IB);

(iii) b) stopping the introduction of aniline in to the reactor IB);

and (iv) operating at least one plant part in such a way that the output stream from the respective plant part is used as feed stream to the respective plant part or an upstream plant part;

(v) shutting down of at least one plant part;

(vi) optionally opening the at least one plant part which has been shut down in step (v);

(vii) optionally performing a maintenance, cleaning, and/or repair measure in the at least one plant part, which has been shut down in step (v); and (viii) optionally closing and optionally making inert the at least one plant part which has been shut down In step (v).

12. The method as claimed in either claim 11, wherein, in step (iv), the output stream in all plant parts which have not been shut down, with the exception of the washing vessel V) and the separation vessel VI), is reused as feed stream for the respective plant part.

13. The method as claimed in claim 11, wherein, to restart the production process for preparing the diamines and polyamines of the diphenylmethane series, all plant parts are started up again after step (viii) in an order which is the reverse of the order of the shutdown or of the changing to recirculation of the output stream from the respective plant part as feed stream to the respective plant part.

* * * * *